(12) United States Patent
Wagener et al.

(10) Patent No.: US 9,173,406 B2
(45) Date of Patent: Nov. 3, 2015

(54) COATING MATERIAL

(75) Inventors: Michael Wagener, Bremen (DE); Dirk Salz, Bremen (DE); Klaus-Dieter Vissing, Morsum (DE)

(73) Assignee: Fraunhofer-Gesellschaft Zur Förderung Der Angewandten Forschung E.V., Munich (DE)

( * ) Notice: Subject to any disclaimer, the term of this patent is extended or adjusted under 35 U.S.C. 154(b) by 209 days.

(21) Appl. No.: 12/936,287

(22) PCT Filed: Apr. 3, 2009

(86) PCT No.: PCT/EP2009/054049
§ 371 (c)(1),
(2), (4) Date: Dec. 3, 2010

(87) PCT Pub. No.: WO2009/121970
PCT Pub. Date: Oct. 8, 2009

(65) Prior Publication Data
US 2011/0104477 A1    May 5, 2011

(30) Foreign Application Priority Data
Apr. 4, 2008 (DE) .................. 10 2008 001 014

(51) Int. Cl.
| B32B 15/04 | (2006.01) |
| B32B 5/16  | (2006.01) |
| B32B 9/00  | (2006.01) |
| A01N 59/16 | (2006.01) |
| A01N 25/00 | (2006.01) |
| A01N 25/08 | (2006.01) |
| A01N 25/10 | (2006.01) |
| A01N 25/34 | (2006.01) |

(Continued)

(52) U.S. Cl.
CPC ............... *A01N 59/16* (2013.10); *A01N 25/00* (2013.01); *A01N 25/08* (2013.01); *A01N 25/10* (2013.01); *A01N 25/34* (2013.01); *A01N 59/20* (2013.01); *A61L 15/44* (2013.01); *A61L 27/54* (2013.01); *A61L 29/16* (2013.01); *A61L 31/16* (2013.01); *C09D 5/14* (2013.01); *C09D 5/1618* (2013.01); *C09D 5/1693* (2013.01); *A61L 2300/102* (2013.01); *A61L 2300/404* (2013.01); *Y10T 428/25* (2015.01); *Y10T 428/256* (2015.01); *Y10T 428/265* (2015.01); *Y10T 428/31678* (2015.04)

(58) Field of Classification Search
None
See application file for complete search history.

(56) References Cited

U.S. PATENT DOCUMENTS

| 5,595,750 A * | 1/1997 | Jacobson et al. ............ 424/421 |
| 6,709,757 B2 * | 3/2004 | Utz et al. .................... 428/448 |

(Continued)

FOREIGN PATENT DOCUMENTS

| DE | 197 58 598 | 4/2000 |
| WO | WO 03/024494 | 3/2003 |

(Continued)

OTHER PUBLICATIONS

Silver, S., "Bacterial silver resistance: molecular biology and uses and misuses of silver compounds," Elsevier Science B.V., FEMS Microbiology Reviews 27 (2003) pp. 341-353.

*Primary Examiner* — Vera Katz
(74) *Attorney, Agent, or Firm* — Preti Flaherty Beliveau & Pachios LLP

(57) ABSTRACT

The invention relates to an antimicrobial and non-cytotoxic coating material and to uses of said coating material.

11 Claims, 3 Drawing Sheets

(51) Int. Cl.

| | | |
|---|---|---|
| *A01N 59/20* | (2006.01) | |
| *A61L 15/44* | (2006.01) | |
| *A61L 27/54* | (2006.01) | |
| *A61L 29/16* | (2006.01) | |
| *A61L 31/16* | (2006.01) | |
| *C09D 5/14* | (2006.01) | |
| *C09D 5/16* | (2006.01) | |

(56) References Cited

U.S. PATENT DOCUMENTS

| | | | |
|---|---|---|---|
| 7,097,912 B2 * | 8/2006 | Aral et al. | 428/516 |
| 7,157,145 B2 * | 1/2007 | Vissing et al. | 428/447 |
| 7,285,335 B2 * | 10/2007 | Aral et al. | 428/516 |
| 7,297,414 B2 * | 11/2007 | Naruse et al. | 428/688 |
| 7,820,284 B2 * | 10/2010 | Terry | 428/323 |
| 2003/0118664 A1 * | 6/2003 | Trogolo et al. | 424/618 |
| 2009/0035341 A1 * | 2/2009 | Wagener et al. | 424/409 |
| 2010/0068438 A1 * | 3/2010 | Yamazaki et al. | 428/36.92 |
| 2010/0173167 A1 * | 7/2010 | Vissing et al. | 428/447 |

FOREIGN PATENT DOCUMENTS

| | | | |
|---|---|---|---|
| WO | WO 2005/049699 | | 6/2005 |
| WO | WO2005048708 | * | 6/2005 |
| WO | WO2008068948 | * | 12/2008 |

* cited by examiner 5-ply 9-ply

COATING MATERIAL

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

BACKGROUND OF THE INVENTION (1) Field of the Invention

The invention relates to an antimicrobial and non-cytotoxic coating material and to uses of said coating material.

(2) Description of Related Art

In many fields, there is a persistent need to control the settlement, reproduction and survival of microorganisms, in particular of prokaryontae and fungi. There is a frequent desire, in particular, to limit the concentration of microorganisms on a certain area, or to keep said area completely free of microorganisms—or of a specific type or species of microorganism in certain cases. This aim is striven for in particular in the medical, medical technological and sanitary-technological fields, in the broadest sense. Antimicrobial materials and coatings, such as silver-coated threads for surgery (see S. Silver, FEMS Microbiology Reviews (2003): pp. 341-353) or anti-fouling paints containing copper, are conventionally used to this end in the field of medical and sanitary products, for example. Broad-spectrum biocides, and inorganic biocides such as silver and its ions, in particular, have proved to be especially effective in this regard. In the course of time, the material treated with the biocide releases the biocide contained within it, and reduces or completely prevents the settlement or reproduction of microorganisms on the material itself, or indeed in its surroundings.

One problem in many cases is that conventional antimicrobial materials initially release a high concentration of biocide, with the consequence that the concentration of the released biocide has a toxic effect not only on the microorganisms being combated, but unintentionally on higher cells as well. This is disruptive in the case of medical products, in particular, such as wound coverings, catheters, contact lenses and implants, because a medical product treated in this way can then delay healing and result in allergies and irritation of tissue. Corresponding disadvantages also arise when biocides are released by sanitary products such as sanitary towels, tampons and diapers, and in the production and processing of foods, especially in the case of biocide-releasing packaging and biocide-releasing components for producing or processing foods. In addition, the antimicrobial effect is rapidly depleted due to leaching from the material containing the biocidic agent.

In order to eliminate these disadvantages, WO 03/024494 proposes an antimicrobial adhesive and coating material containing metallic silver particles with a silver, sodium and potassium ion concentration of less than 5 ppm, the adhesive and coating material being a synthetically produced organic material that is generally hardened after processing. The silver particles are uniformly distributed in the adhesive and coating material. Specifically, the adhesive and coating material should be a varnish or adhesive, particularly a thermoset or thermoplastic varnish or adhesive. One disadvantage of the latter, however, is that the rate of metal ion release is difficult to control or adjust.

BRIEF SUMMARY OF THE INVENTION

It was therefore an object of the present invention to define a coating material having antimicrobial properties that is simple and inexpensive to produce, but which should not be cytotoxic. A coating material is deemed to be antimicrobial if it inhibits the reproduction of *Staphylococcus epidermidis* for at least ten hours, measured as described in DE 197 58 598 A1. A coating material is also considered cytotoxic when it has a cytotoxic effect as described in the DIN-ISO 10993-5 standard. In addition, the coating material should also have an antimicrobial and non-cytotoxic effect of maximum possible persistence. It should be usable as universally as possible and also allow the production of thin coatings.

The invention therefore proposes an antimicrobial and non-cytotoxic coating material, comprising:

a) a carrier layer;
b) at least one biocide layer containing a biocidic agent applied to the carrier layer, and
c) a transport control layer applied to a biocide layer with a gas permeability for oxygen ($O_2$) of between 50 and less than 100 $(cm^3\ bar)/(day\ m^2)$.

BRIEF DESCRIPTION OF THE SEVERAL VIEW OF THE DRAWINGS

FIG. 1: A cross-section of an antimicrobial and non-cytotoxic coating material.

FIG. 2: Plots of bacterial growth on various polyurethane surfaces.

DETAILED DESCRIPTION OF THE INVENTION

Figure 1:
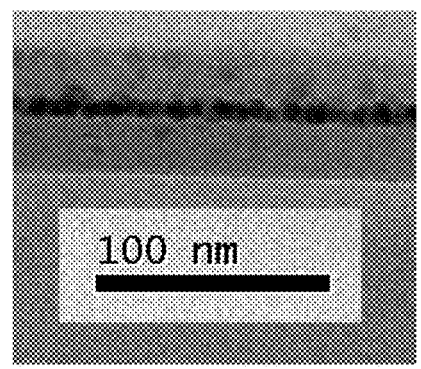

With the gas permeability for oxygen of the transport control layer selected according to the invention it is possible to release the biocidic agent from the biocide layer through the transport control layer in an antimicrobially effective and simultaneously non-cytotoxic quantity. Compared to conventional antimicrobial materials, the coating material according to the invention allows a high biocide concentration that would normally be cytotoxic to be provided in the coating material itself. The biocide layer forms a depot of the biocidic agent, so to speak, in order to allow protracted release of the biocidic agent. By providing the transport control layer with the abovementioned gas permeability it is also possible for the concentration of biocidic agent released from the biocide layer through the transport control layer to be restricted to such an extent that the agent is no longer cytotoxic, yet at the same time still has an antimicrobial effect. The transport control layer thus has a controlling and regulating function. Furthermore, the transport control layer can prevent any direct contact between the surroundings and the biocide layer. The durability of the coating material is enhanced as a result. The transport control layer can be disposed on both sides or only on one side of the biocide layer. The latter is particularly preferred whenever the coating material according to the invention forms a coating on a solid body. In such a case, the solid coated with the coating material according to the invention can cover the side of the biocide layer that is not covered by the transport control layer.

A biocidic agent within the meaning of the present invention is any substance that can develop an antimicrobial effect in the sense described above (a biocidic agent in the narrower sense). The category of biocidic agents also includes substances that produce the biocidic agent in the narrower sense by converting in the environment in which a coating material is to be used. For example, if the biocidic agent in the narrower sense is a metal ion, in particular a silver, copper and/or zinc cation, then metallic silver, copper and/or zinc as well as alloys, complexes and other such substances are biocidic agents from which said cations can be released into an appropriate environment, for example in the area of a wound.

Surprisingly, it now transpires that in particular when silver is used as the biocidic agent through the oxygen gas permeability selected a particularly long-lasting antimicrobial effect of the coating can be achieved. This was all the more surprising because it was expected that water, which is necessary for the release of silver ions from particulate silver, would not be able to pass through the transport control layer in sufficient quantity, such that an adequate antimicrobial effect could not be expected.

The person skilled in the art understands that a coating material according to the invention can also have antimicrobial effects against other microorganisms, and not or not only against *Staphylococcus epidermidis*. The antimicrobial efficacy of the coating material according to the invention is measured in respect of other microorganisms in accordance with DE 197 58 598 A1 using the respective microorganism in place of *Staphylococcus epidermidis*. Particularly preferred are coating materials according to the invention which, without being cytotoxic, have an antimicrobial effect against one or more of the microorganisms in the group consisting of *Bacillus, Clostridium, Enterobacter, Escherichia, Pseudomonas, Salmonella, Staphylococcus, Yersinia* and *Candida*.

The biocidic agent can be embedded in the transport control layer and/or in the carrier layer in order to form a biocide layer. In preferred embodiments according to the invention the coating material therefore contains a particulate biocidic agent, in particular particulate silver, with the individual particles being embedded in the carrier layer and/or the transport control layer.

The biocidic agent and in particular silver as the bactericide are preferably present in the form of particles, in some cases if necessary melded together, as obtainable from vacuum evaporation, sputtering and chemical vapor deposition as described in further detail below. Here the particles are solid particles and not carrier particles coated with the biocidic agent.

The transport control layer of the coating material according to the invention is preferably designed to have a gas permeability for oxygen ($O_2$) of less than 100 ($cm^3$ bar)/(day $m^2$), preferably of between 50 and less than 100 ($cm^3$ bar)/(day $m^2$). Such transport control layers can be produced in a particularly appropriate manner using plasma polymerization. On the basis of the gas permeability criterion described above, the person skilled in the art can, in carrying out the usual routine tests, identify suitable starting materials and parameters for producing a corresponding transport control layer. Particularly preferred transport control layers are defined in the rest of this description and in the examples.

The transport control layer can be produced with the help of vacuum engineering. For vaporizable, organic compounds in particular the plasma polymerization (PE-CVD) method is suitable for depositing a transport control layer on a substrate. Examples of organic compounds are saturated or unsaturated linear or cyclical hydrocarbons which can if necessary have additional functionalities (e.g. substituents). These optional functionalities preferably contain heteroatoms, with particular preference being for hydroxyl or carboxyl groups or amines. Apart from organic compounds, metal-organic compounds can be used to produce a transport control layer by plasma polymerization. In this connection the depositing of titanium oxide and vanadium oxide is particularly preferred; in such cases the transport control layer is particularly preferably produced through the plasma-based polymerization of titanium isopropoxide or vanadium triisopropoxide. If the vapor pressure of the metal-organic compound is increased by heating, then tungsten oxides can be produced from tungsten methoxide and tin oxide from the non-toxic tetravinyl tin.

The transport control layer can also be deposited by sputtering, with the use of a direct (DC), medium (MF) and high frequency (HF) voltage being possible. For the depositing of oxide layers (e.g. titanium oxide, hafnium oxide) the metallic target is sputtered in reactive DC sputter mode in an Ar/O2 atmosphere. Alternatively, however, the high frequency mode can also be used. Apart from oxides, in principle carbides, sulfides, titanates, vanadates, tungstates, selenates and molybdates can be used. Here a cathode material is used corresponding to the coating material. Since the compounds mentioned above may be isolators, such coatings can be sputtered with a high frequency voltage. However, in general there is no coating material that corresponds to the chemical composition of the target material. Deviations from the stoichiometry are normal with this methodical approach.

Apart from their antibacterial, non-cytotoxic characteristics, other layer functions can have an important role to play. In the case of implants which must have a high mechanical wear resistance, a high layer hardness is required and this can be achieved with the transport control layer according to the invention. The coating material according to the invention and in particular the transport control layer preferably has a hardness of more than 1 GPa in nanoindentation measurements.

It is also preferred if the surface energy, which influences the cell adhesion, is 40-110 mN/m. Particular preference in the case of long-term stability surfaces is for surface energies of 50-110 mN/m. For dirt-repellant coating materials the surface energy is less than 30 mN/m. This surface characteristic can be adjusted if necessary by a very thin additional coating.

The usage time of the coating or the period over which the bactericide is to be released, can be extended by the disposition of a plurality of biocidic and transport control layers directly on top of one another (multilayer). In this connection particular preference is for a coating with the structure $Ag/SiO_2/Ag/SiO_2/Ag/SiO_2/Ag/SiO_2$, as compared with the $Ag/SiO_2$ coating this has a markedly longer antibacterial effect. The possibility also exists of adjusting the color of the coating through the selection of the layer structure. If two $Ag/SiO_2$ layers are deposited one on top of the other and the color of the first coating is yellow and that of the second is blue, then the resulting color of the coating as a whole is green.

In many, specifically medical, applications, the sterilizability of the coated substrate is an important basic prerequisite for its usability. The layer structure or the packing must be selected so that the coating by gamma radiation and autoclaving or by treatment with ethylene oxide does not lead to the failure of the coating. Layers that lend themselves to sterilization by autoclaving or with ethylene oxide must have good bonding to the substrate. Pretreatment of the substrate in the oxygen plasma is therefore particularly preferred with this application area.

It is also necessary to consider that in order for autoclaving to be possible the coating should be heat-resistant to at least 200° C. Virtually all oxides and many highly cross-linked purely organic layers have such heat resistance. The person skilled in the art, in the knowledge of this invention, if necessary with the help of his general technical knowledge, can broaden the production methods presented in this description and in the examples for transport control layers and their materials in order to readily develop transport control layers with other materials and/or production methods through routine work.

Particular preference is for coating materials according to the invention, in which the biocidic agent is an inorganic biocide. Such biocidic agents are normally inexpensive, readily available and easy to process. The biocidic agent can be prepared by various methods. In particular it can be applied to a surface which is to be coated with a coating material according to the invention. Vacuum evaporation, sputtering and chemical vapor deposition are particularly suitable for the application of an inorganic biocidic agent.

In one particularly preferred embodiment of the coating material according to the invention, the biocidic agent is selected from the group consisting of silver, copper and zinc, their ions and their metal complexes, or a mixture or alloy of said elements. These biocidic agents are effective against many different microorganisms and attack their metabolism in numerous ways. Thus it is rarer for bacteria to become resistant when these biocides are used than when organic biocides with specific mechanisms of action, particularly antibiotics, are used.

It has been found that a particularly advantageous coating material according to the invention is one in which the biocidic agent is silver, a silver cation, or a complex or alloy which releases silver or silver cations. Metallic silver, in particular, can be easily processed and is available in high quality at a relatively low price, with the result that the coating material according to the invention can be produced relatively inexpensively.

It is expedient if the biocidic agent is present in granular form in the coating material according to the invention, the primary particles preferably having a mean particle size of 5-100 nm. Biocidic agents in such fine powdery form can be easily produced, particularly for inorganic biocides and for silver in particular, but also for copper and zinc, as well as mixtures, complexes and alloys of said three metals. The biocidic agent has a high specific surface due to the mean particle size being so small, so it can be released well by diffusion from the biocide layer. Another advantageous aspect is that, because of the high specific surface, chemical inactivation of the granular agent, as sometimes required in the wound surroundings, usually affects only part of the surface, thus enabling release of the biocidic agent from the biocide layer even under adverse conditions. Coating materials according to the invention in which the mean particle size of the biocidic agent is 5-50 nm, preferably 5-20 nm, have been found to be especially advantageous. When the biocidic agent is silver or a silver alloy, these particle size distributions are also referred to as nanoscale silver or nanoscale silver alloys.

When using silver, copper and zinc, their ions and their metal complexes or a mixture or alloy of said elements as a biocidic agent it is particularly preferable if the biocidic agent does not have any direct contact with an electrically conductive substrate. It is therefore preferred in particular in the event that the coating according to the invention is to be applied to a metal substrate such as for example stainless steel, titanium or titanium alloys, by means of the carrier layer, to create an electrically insulating separation between the biocidic agent and the substrate.

Depending on the area of application, the biocide layer can have a thickness of at least 1 nm and preferably of at least 3 nm, and more preferably of not more than 1 mm and preferably not more than 100 nm. If the coating material comprises a plurality of layers, then these thicknesses apply to each individual biocide layer. The biocide layer—apart from the presence of the biocidic agent—need not consist of a different material from the carrier layer and/or the transport layer, rather the biocidic agent can also be embedded in one or between both layers. Then the term "thickness of the biocide layer" means the thickness of the area of the carrier layer and/or of the transport control layer in which the biocidic agent is embedded. When using granular biocidic agents, the biocide layer is therefore at least as thick as the granular agent. The thickness of the biocide layer is preferably 1 nm to 100 nm, layer thicknesses of 3 nm to 50 nm being particularly preferred, in particular when the biocidic agent is silver, copper and/or zinc or their ions, metal complexes or a mixture or alloy of said elements. It has been found that, in a coating material according to the invention, even such thin layers of a biocidic agent (in particular of a biocidic agent containing nanoscale silver) are sufficient to be able to achieve a persistent antimicrobial and non-cytotoxic effect.

Also preferred is a coating material according to the invention in which the biocide layer also comprises: gold, platinum, palladium, iridium, tin, antimony, their ions, their metal complexes, or a mixture or alloy of the biocidic agent with one or a plurality of said elements. Adding said elements to the biocidic agent increases and/or prolongs its antimicrobial efficacy. The aforesaid elements are preferably bonded in cationic form in ion exchangers, in the form of a complex or a salt, preferably of a polymeric carboxylic acid.

Also preferred is a coating material according to the invention wherein the transport control layer and/or the carrier layer has a base material that is selected from the group consisting of
a) an organic base material, in particular a plasma polymer, a sol-gel, a lacquer, and a siliconized base material, or
b) an inorganic base material, in particular $SiO_2$ and SiC, a metal oxide, in particular $TiO_2$ and $Al_2O_3$, and a non-biocidic metal, in particular titanium or medical stainless steel.

It is understood here that the base material has a thickness and porosity that enable the biocidic agent to be released through the transport control layer in a concentration at which the biocidic agent thus released can act antimicrobially and non-cytotoxically. Here it is particularly preferred for the base material to be microporous. It is preferred, especially when producing thin layers, to produce the transport control layer using a plasma polymerization method or sputtering. It is possible in this way to produce very thin transport control layers through which the biocidic agents, such as atomic or cationic silver, for example, can diffuse and confer on the coating material its antimicrobial, non-cytotoxic activity.

The transport control layer is preferably produced in such a way that its layer thickness, density, moisture uptake capacity, diffusion tightness against water vapor, its chemical composition and its cross-linkage structure enable the biocidic agent to be released through the transport control layer, such that the biocidic agent thus released can have antimicrobial and non-cyclotoxic effects. If a plasma polymer layer serves as transport control layer, for example, this layer preferably has strong cross-linkings and a low specific permeability for water vapor and a low moisture absorption capacity. A transport control layer of this kind requires only a very small layer thickness to ensure that the biocidic agent still has sufficient antimicrobial effectiveness but no cytotoxic effects.

A particularly preferred coating material according to the invention is one in which the carrier layer and/or transport control layer has a silicon content of 20-60%, a carbon content of up to 10-30% and an oxygen content of 30-50%. It is understood here that the proportions must be matched to each other in such a way that they do not exceed 100% in total. Here the proportions are measured using X-ray photoelectron spectroscopy (XPS); when determining the silicon, carbon and oxygen content, elements are ignored here that cannot be determined using XPS analysis, such as hydrogen, for example. Thus, in addition to silicon, carbon and oxygen, there may be other elements present in the carrier layer and/or transport control layer (namely elements that cannot be detected with XPS), without these additional elements being taken into consideration when determining the silicon, carbon and oxygen content. The silicon, carbon and oxygen content is expressed as atomic or molar percentages of the elements detectable with XPS analysis.

The carrier layer and/or transport control layer of a coating material according to the invention preferably has a mean thickness of 5 nm to 500 nm. In particular when using a plasma polymer carrier layer and/or plasma polymer transport control layer, however, it is preferred that the carrier layer and/or transport control layer has a thickness of 5-200 nm, preferably 10-100 nm. With layer thicknesses of this order, it is possible, especially with carrier layers and/or transport control layers produced by plasma polymerization, to produce outstanding antimicrobial and non-cytotoxic coating materials. These carrier layers and/or transport control layers are also very thin, so they are visually inconspicuous and may even be transparent.

It is particularly advantageous when the biocide layer and carrier layer and/or transport control layer all have the same base material. In this way, it is possible in particular to provide firstly a biocidic agent (in particular silver, copper and/or zinc) in preferably nanoscale form on a carrier layer and then, if desired, by applying the base material to a further carrier layer, to apply one or more further biocide layers. Then it is possible by applying the base material of the transport control layer in a single further step, to produce the coating material according to the invention and in doing so to embed the biocidic agent in said coating material.

The base material of the transport control layer can also be selected so that the transport control layer has additional and advantageous properties on top of its enabling the biocidic agent to be released through the transport control layer. In particular, by selecting a suitable base material or by means of other measures, the transport control layer can be made transparent, hydrophilic, hydrophobic and/or non-adhering (also for bacteria).

It is particularly preferred if the carrier layer and the transport control layer have the same base material.

In accordance with the invention a coating material is also preferred which comprises a plurality of carrier layers and biocide layers, so that at least one biocide layer is embedded between two carrier layers. In this way the coating material can comprise a higher content of biocidic agent than would be achievable through embedding in a single layer. In particular if the biocidic agent is a particulate agent it may be that the thickness of the biocide layer may not exceed a maximum thickness dependent upon the base material of the carrier layer and/or the transport control layer without the coating material causing damage to the mechanical stability and in particular to the wear resistance. By using a plurality of biocide layers, none of which exceeds the maximum thickness, it is possible to increase the content of biocidic agent in the coating material according to the invention without significant damage to the mechanical stability.

Here it would have been expected that by increasing the thickness of the coating material according to the invention and accordingly by increasing the distance between the outer surface of the transport control layer and the biocide layer furthest away from it, the diffusion of the biocidic agent from this biocide layer to the surface of the transport control layer would be impeded too much to allow continued release of the biocidic agent. If diffusion were possible, however, the fear would be that by increasing the content of biocidic agent, the coating material would release the agent in a higher and therefore cytotoxic quantity. Surprisingly, however, it has been found that the biocidic agent, even from from the biocide layer furthest away, still reaches the surface of the transport control layer and has an antimicrobial and non-cytotoxic effect there.

Particularly preferred carrier layer and transport layer combinations are:

$SiO_2$/Ag/$SiO_2$; $TiO_2$/Ag/$TiO_2$; organic coating/Ag/organic coating; coating systems with silver and anti-glare effect.

The biocide layer and the coating material according to the invention, in its entirety, can be present in any form. In particular, the biocide layer and the coating material according to the invention can form a coating on a solid body, for example on a fiber or on a metal, plastic and/or glass surface. However, the biocide layer and the coating material according to the invention can also form a coating on particles.

When silver (in particular nanoscale silver) is used as the biocidic agent, the silver content of the coating material according to the invention is preferably 1-100 ppm. It has been found, surprisingly, that solid silver in a coating material according to the invention can develop a sufficiently antimicrobial effectiveness even in the quantities cited.

According to the invention, the coating material described in the foregoing, including its embodiments, can be used to produce an antimicrobial and non-cytotoxic coating on a solid body. In particular, it can be used to produce an antimicrobial and non-cytotoxic coating on a medical product, in particular a catheter, a wound covering, a contact lens, an implant, a medical nail and/or screw, bone fixation nails, a medical instrument, or on a sanitary product, in particular a sanitary towel, a tampon or a diaper, or on the packaging of a medical or sanitary product, or on a component for producing or processing foodstuffs, or on another product for which particular hygiene is required. As described at the beginning, there is a need in particular in the field of medical and sanitary products for products that are antimicrobial yet non-cytotoxic. By providing conventional products with a coating material according to the invention—for example by coating them with said coating material—this need can be met in a very simple manner.

The invention will now be described in greater detail with reference to preferred embodiments.

Example 1

Production of a coating material according to the invention

In a vacuum at $1.5*10^{-2}$ mbar a polystyrene substrate of $25\times10\times10$ $mm^3$ undergoes plasma fine purification ($O_2$ flow=100 sccm, P=1000 W, t=10 min). Then a $SiO_2$ coating is performed using a HMDSO/$O_2$ plasma (HMDSO flow=10 sccm, $O_2$=100 sccm, P=1000 W). Following a deposition time of 10 min a layer of approximately 50 nm in thickness is produced on the substrate. Silver particles are applied to this layer under an $H_2O$ partial pressure of $5*10^{-3}$ mbar using an HF sputter source. The sputter time is 10 minutes and the sputter power 1000 W. The transport control layer is produced in the same way as the first $SiO_2$ layer again by plasma polymerization at a pressure of 0.015 mbar, a plasma power of 1,000 W, an HMDSO flow of 10 sccm and an $O_2$ flow of 100 sccm. After 10 minutes deposition time an approximately 50 nm thick $SiO_2$ layer results as the transport control layer. The TEM image of this coating is shown in FIG. 1.

Example 2

Production of a Coating Material According to the Invention

For the production of a 5-ply or 9-ply layer system on a metal rod with a length of 20 cm and a diameter of 5 mm initially plasma fine purification is carried out using the parameters of Example 1. Then depositing takes place of a $SiO_2$ coating and the silver particles, again as described in Example 1. If these two coatings are repeated once, then following the final coating with the transport control layer the 5-ply layer system results ($SiO_2$/Ag/$SiO_2$/Ag/$SiO_2$), and after four repetitions the 7-layer system ($SiO_2$/Ag/$SiO_2$/Ag/$SiO_2$/Ag/$SiO_2$/Ag/$SiO_2$). Following preparation a SIM depth profile of these layers was taken.

Figure 3:
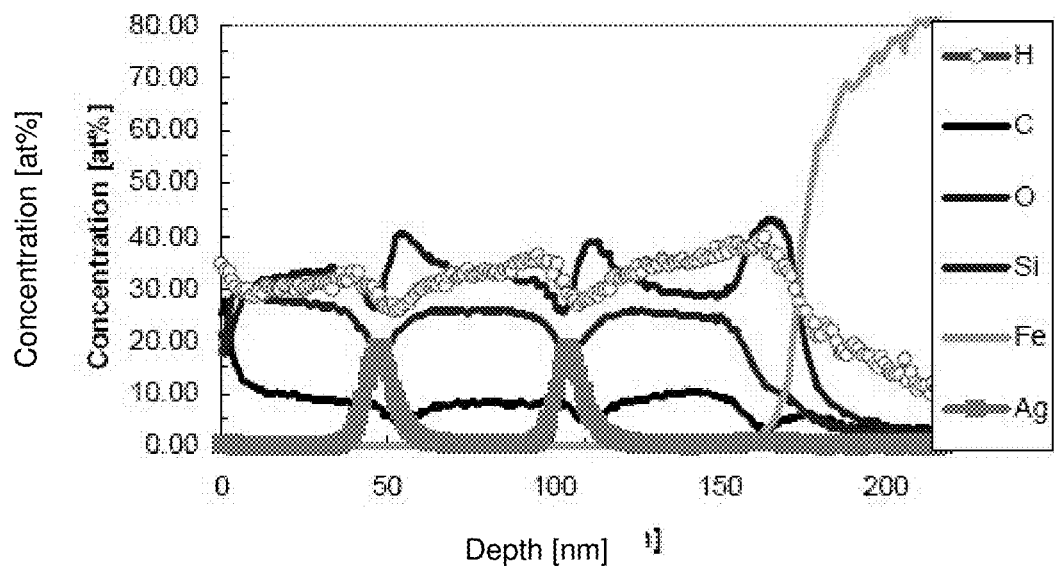
FIG. 3 shows a SIMS depth profile of a 5-ply layer from Example 2.

FIG. 3 shows a SIMS depth profile of a 5-ply layer from Example 2. Here "Concentration" means the quantity of elements determined in atom-%, "Depth" means the distance from the surface of the metal rod in nm. Example 5 explains the figure in more detail.

Figure 4:
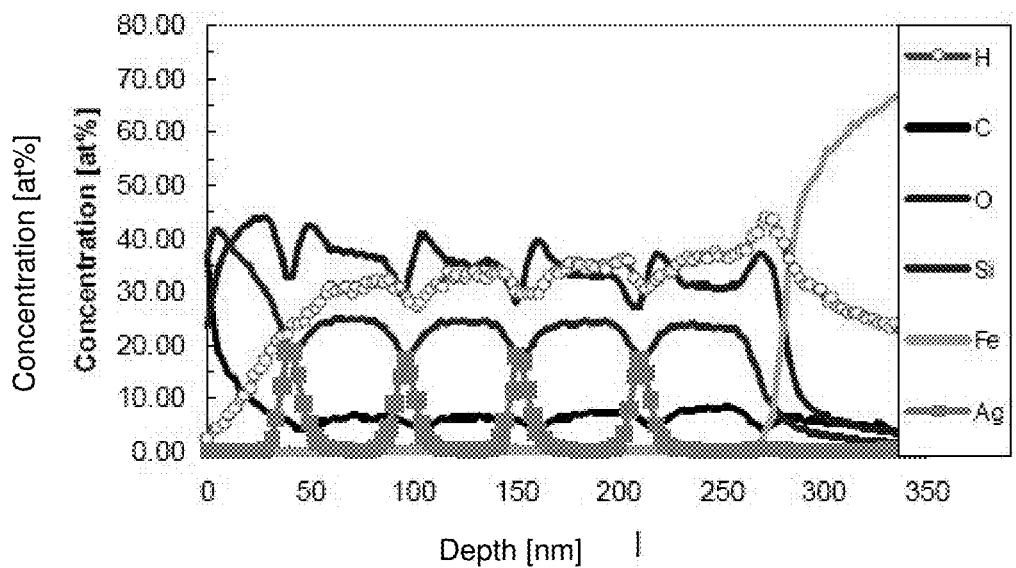
FIG. 4 shows a SIMS depth profile of a 9-ply layer system from Example 2.
Figure 5:
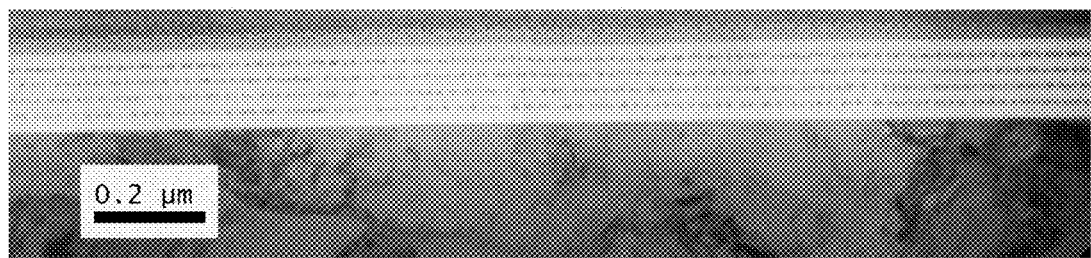
FIG. 5 shows a TEM image of the 9-ply layer system.

FIG. 4 shows a SIMS depth profile of a 9-ply layer system from Example 2. Here "Concentration" again means the quantity of elements determined in each case in atom-%, and "Depth" means the distance from the surface of the metal rod in nm. Example 5 explains the figure in more detail. FIG. 5 shows a TEM image of the 9-ply layer system.

The method described in Example 2 can be used to coat medical products in particular, such as wound dressings, bone nails and catheters with a coating material according to the invention.

Example 3

Production of a Further Coating Material According to the Invention

A substrate to be provided with a coating material according to the invention is provided in an initial processing stage with a titanium dioxide film through plasma polymerization. Titanium tetraisopropyloxide (TTIP) mixed with oxygen is used as the precursor. The polymerization time is five minutes. The result is a 25 nm thick $TiO_2$ film with good adhesion. Silver particles are applied to this layer under an $H_2O$ partial pressure of $5*10^{-3}$ mbar using an HF sputter source. The sputter time is 10 min and the sputter power 1,000 W. In a third coating step a plasma polymer layer (transport layer) is applied to the silver layer. The plasma polymerization again takes place using TTIP mixed with oxygen. The layer system as a whole thus consists of a $TiO_2$/Ag/$TiO_2$ structure. The titanium oxide can also be activated by UV radiation, i.e. the surface energy experiences a strong temporary increase (above 72 mN/m).

The following materials lend themselves well to application of the coating material according to the invention: metals, in particular titanium and (as appropriate medical) stainless steel, plastics, in particular polyurethane, and cellulose, in particular wound dressings and cellulose fleeces.

Example 4

Production of a Further Coating Material According to the Invention

In Example 3 the $TiO_2$ layers are produced by plasma polymerization of the titanium organic precursor TTIP. Alternatively titanium oxide can also be prepared by reactive magnetron sputtering. For this sputtering takes place under an Ar/$O_2$ atmosphere ($O_2$P partial pressure=$7.10^{-5}$ mbar) of a metal Ti target at a DC sputter power of 4 kW. The static layer deposition rate with this process is approximately 30 nm/min.

Example 5

Investigation of a Layer Material Produced According to Example 2

The 5-ply (FIG. 3) and the 9-ply (FIG. 4) layer systems from Example 2 were investigated using Secondary Ion Mass Spectrometry (SIMS). For this a hole is fired in the coating with a targeted Ar ions beam. The material removed (sputtered) here is analyzed by SIMS. Through continuous operation of the Ar ion source and of the SIMS a depth-related element analysis is possible. $SiO_2$ was selected as the reference material, because the oxygen component in the coating has a similarly high oxygen content. The elements hydrogen (H), oxygen (O), silicon (Si), silver (Ag), iron (Fe) and carbon (C) were recorded.

The overall layer thickness of the 5-ply layer was approximately 150 nm and that of the 9-ply layer approximately 250 nm. Here the thickness of the coating was measured from the surface of the coating to the depth at which the iron signal increased. The individual $SiO_2$ layers in each case had a thickness of approximately 50 nm, each separated by a 10 nm silver layer. The silver concentration of the individual Ag layers was approximately the same.

Figure 2:
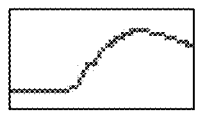
Figure 2:
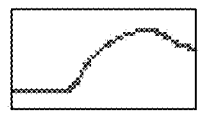
Figure 2:
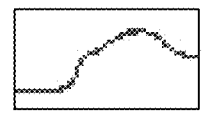
Figure 2:
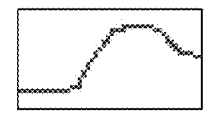
Figure 2:
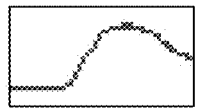
Figure 2:
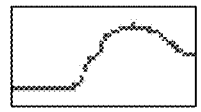
Figure 2:
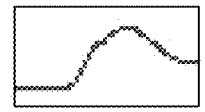
Figure 2:
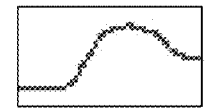

FIG. 2 provides evidence of the antimicrobial effect of a polyurethane surface provided with a coating material according to the invention after Example 1 compared with an untreated polyurethane surface. The antimicrobial effect was tested as described in DE 197 58 598 A1 with *Staphylococcus epidermidis*. FIG. 2 shows the change in optical density and thus the bacterial count over a period of 48 hours. The bacterial growth development of the 5-ply layer and the 9-ply layer described above is shown for 4 independent trials in each case.

On an untreated polyurethane surface bacterial growth (not shown) occurs within a very short period of time, while on the coating materials according to the invention within the timeframe shown a markedly slower bacterial growth occurs. Accordingly, the coating material according to the invention is antimicrobial. According to DIN-1S010993-5 it is also non-cytotoxic (no figure provided).

The invention claimed is:
1. An antimicrobial and non-cytotoxic coating material, comprising:
   a) a carrier layer having a base material;
   b) at least one biocide layer containing a biocidic agent applied to the carrier layer; and
   c) a transport control layer applied to a biocide layer with a gas permeability for oxygen ($O_2$) of between 50 and less than 100 ($cm^3$ bar)/(day $m^2$);

wherein the biocidic agent is an inorganic biocidic agent;
wherein the transport control layer and the carrier layer each has a base material;
wherein the base material of the transport control layer has the same composition as the base material of the carrier layer;
wherein the base material of each of the transport control layer and the carrier layer is selected from the group consisting of:
a) an organic base material, and
b) an inorganic base material of $Al_2O_3$ and a non-biocidic metal; and
wherein the coating material comprises a plurality of carrier layers and biocide layers, so that at least one biocide layer is embedded between two carrier layers.

2. The antimicrobial and non-cytotoxic coating material of claim 1, wherein the organic base material is selected from the group consisting of a plasma polymer, a sol-gel, a lacquer, and a siliconized base material.

3. The coating material as claimed in claim 1, wherein the carrier layer is configured to be disposed directly on a solid substrate.

4. The coating material as claimed in claim 1, wherein the transport control layer has a gas permeability for oxygen ($O_2$) of between 80 and less than 100 ($cm^3$ bar)/(day $m^2$).

5. The coating material as claimed in claim 1, wherein the biocidic agent comprises a first substance selected from the group consisting of silver, copper, zinc, their ions, their metal complexes, and a mixture comprising at least two of the first substances.

6. The coating material as claimed in claim 1, wherein the biocidic agent has a mean particle size of 5-100 nm.

7. The coating material as claimed in claim 1, wherein in addition to the biocide agent the biocide layer further comprises a second substance containing at least one of gold, platinum, palladium, iridium, tin, antimony, their ions, their metal complexes, and an alloy of the biocidic agent and at least one of the second substance.

8. The coating material as claimed in claim 1, wherein the transport control layer has a silicon content of 20-60%, a carbon content of 10-30% and an oxygen content of 30-50%.

9. The coating material as claimed in claim 1, wherein the biocide layer has an average thickness of 5-100 nm.

10. The coating material as claimed in claim 1, wherein the transport control layer has an average thickness of 5-500 nm.

11. A coating material comprising:
a) a carrier layer having a base material;
b) at least one biocide layer containing a biocidic agent applied to the carrier layer; and
c) a transport control layer applied to a biocide layer with a gas permeability for oxygen ($O_2$) of between 50 and less than 100 ($cm^3$ bar)/(day $m^2$);
wherein the biocidic agent is an inorganic biocidic agent comprising a first substance selected from the group consisting of silver, copper, zinc, their ions, their metal complexes, and a mixture comprising at least two of the first substances;
wherein the transport control layer and the carrier layer each has a base material;
wherein the base material of the transport control layer has the same composition as the base material of the carrier layer;
wherein the biocidic agent has a mean particle size of 5-100 nm;
wherein the biocide layer comprises a second substance selected from the group consisting of gold, platinum, palladium, iridium, tin, antimony, their ions, their metal complexes, and an alloy formed from the biocidic agent and one or more of the second substances;
wherein the base material of each of the transport control layer and the carrier layer is selected from the group consisting of
a) an organic base material, and
b) an inorganic base material and a non-biocidic metal;
wherein the transport control layer has a silicon content of between 20-60%, a carbon content of between 10-30% and an oxygen content of between 30-50%;
wherein the biocide layer has an average thickness of between 5-100 nm;
wherein the transport control layer has an average thickness of between 5-500 nm;
wherein the carrier layer has a silicon content of 20-60%, a carbon content of 10-30% and an oxygen content of 30-50%; and
wherein the coating material comprises a plurality of carrier layers and biocide layers, so that at least one biocide layer is embedded between two carrier layers.

* * * * *